(12) United States Patent
Green

(10) Patent No.: US 6,217,554 B1
(45) Date of Patent: Apr. 17, 2001

(54) METHODS AND APPARATUS FOR DELIVERING SUBSTANCES INTO EXTRAVASCULAR TISSUE

(75) Inventor: Bert Green, Seattle, WA (US)

(73) Assignee: PharmaSpec Corporation, Redmond, WA (US)

( * ) Notice: Subject to any disclaimer, the term of this patent is extended or adjusted under 35 U.S.C. 154(b) by 0 days.

(21) Appl. No.: 09/249,751

(22) Filed: Feb. 12, 1999

(51) Int. Cl.[7] .................................................. A61M 5/178
(52) U.S. Cl. ............................... 604/164.01; 604/164.01; 604/532; 604/506; 604/511; 604/264
(58) Field of Search ..................... 604/264, 48, 500, 604/506, 507–509, 93, 96, 158, 523, 529, 530

(56) References Cited

U.S. PATENT DOCUMENTS

| | | | |
|---|---|---|---|
| 5,088,979 | 2/1992 | Filipi et al. ........................... | 604/26 |
| 5,354,279 | * 10/1994 | Höfling ................................. | 604/164 |
| 5,419,777 | 5/1995 | Höfling ................................. | 604/264 |
| 5,464,395 | * 11/1995 | Faxon et al. ........................... | 604/96 |
| 5,536,267 | 7/1996 | Edwards et al. ...................... | 606/41 |
| 5,672,174 | 9/1997 | Gough et al. ......................... | 606/41 |
| 5,693,029 | 12/1997 | Leonhardt ............................. | 604/264 |
| 5,713,853 | * 2/1998 | Clark et al. ........................... | 604/53 |
| 5,728,143 | 3/1998 | Gough et al. ......................... | 607/101 |
| 6,004,295 | * 12/1999 | Langer et al. ........................ | 604/164 |

FOREIGN PATENT DOCUMENTS

| | | | |
|---|---|---|---|
| 2124684 | * 11/1972 | (DE) ........................................ | 604/53 |
| 63-275632 | 10/1988 | (JP) ................................. | A61N/5/02 |

OTHER PUBLICATIONS

Fleischer, K.J. et al., "One–Month Histologic Response of Transmyocardial Laser Channels With Molecular Intervention," *Ann. Thorac. Surg.*, 62:1051–1058 (1996).

Schumacher, B. et al., "Induction of Neoangiogenesis in Ischemic Myocardium by Human Growth Factors," *Circulation*, 97:645–650 (1998).

* cited by examiner

Primary Examiner—Richard K. Seidel
Assistant Examiner—Jennifer Maynard
(74) Attorney, Agent, or Firm—Ronald M. Anderson

(57) ABSTRACT

Apparatus and methods for delivering a therapeutic or diagnostic agent into extravascular tissue surrounding a body passageway is provided comprising a catheter having a sheath, a tubular member, and a plurality of hollow needles on a distal end of the tubular member. The tubular member is selectively movable between delivery position, wherein the plurality of hollow needles are retracted within the sheath, and an extended position, wherein the plurality of hollow needles extend beyond a distal endface of the sheath to pierce and penetrate extravascular tissue. The catheter also includes a balloon for applying pressure to seal puncture wounds created by the hollow needles.

20 Claims, 2 Drawing Sheets

METHODS AND APPARATUS FOR DELIVERING SUBSTANCES INTO EXTRAVASCULAR TISSUE

FIELD OF THE INVENTION

The present invention relates to apparatus and methods for delivering a therapeutic or diagnostic agent into extravascular tissue. More particularly, the present invention provides a catheter for delivering therapeutic or diagnostic materials to cardiac tissue using the cardiac vasculature.

BACKGROUND OF THE INVENTION

A number of techniques have been developed to treat occlusive diseases of the heart, such as atherosclerosis. For example, stenosis of the coronary arteries typically is treated using bypass grafting techniques. More recently, minimally-invasive techniques, such as percutaneous transluminal angioplasty and atherectomy, have been developed that use catheter-based systems to disrupt or remove a stenosis. Techniques such as transmyocardial revascularization ("TMR") also have been developed, in which a high-energy laser is used to ablate a matrix of channels in the myocardial tissue to enhance perfusion.

More recently, attempts at stimulating revascularization of cardiac tissue have focused on the use of the angiogenic factors. For example, Schumacher et al., "Induction of Neoangiogenesis in Ischemic Myocardium by Human Growth Factors," *Circulation* 97:645–650 (1998), report that intraoperative injection of fibroblast growth factor (FGF-I) into the myocardium of 20 patients suffering from stenosis of the internal mammary artery/left anterior descending coronary artery resulted in the development of new capillary vessels radiating outward from the injection point in 4 days.

By comparison, however, Fleischer et al., "One-Month Histologic Response of Transmyocardial Laser Channels With Molecular Intervention," *Ann. Thorac. Surg.*, 62:1051–8 (199), report that a single dose of vascular endothelial growth factor (VEG-F), administered intraoperatively at the time of laser TMR, showed no significant increase in myocardial vascularity. It was hypothesized that longer residence of the VEG-F may be required to stimulate angiogenesis.

In view of the foregoing, it would be desirable to provide methods and apparatus for percutaneously injecting therapeutic agents, such as drugs or angiogenic growth factors, into myocardial tissue to promote revascularization.

It also would be desirable to provide methods and apparatus for percutaneously injecting diagnostic agents, such as radio-isotopes or contrast agents, into myocardial tissue to enhance diagnosis of cardiac ischemia.

Apparatus and methods are known for injecting pharmacological agents into the walls of vessels, and surrounding tissue, to reduce restenosis following the use of minimally-invasive techniques, such as angioplasty. For example, angioplasty balloons often injure a large percentage of the endothelium that they contact, and the healing response may itself lead to recurrence of the stenosis. Methods and apparatus therefore have been developed for injecting drugs, such as anti-platelet, anti-coagulant, anti-proliferative and/or anti-inflammatory drugs, into the wall of a treated vessel, or adjacent tissue, to discourage restenosis.

For example, U.S. Pat. No. 5,464,395 to Faxon et al. describes a system for delivering therapeutic or diagnostic agents to tissue surrounding a vessel. A needle cannula having a tissue-piercing tip is extended from a delivery catheter to penetrate a selected distance into tissue surrounding the vessel to inject a therapeutic or diagnostic agent. The device includes a balloon for dilating the vessel prior to extending the needle cannula. If multiple needle cannulas are used, each needle cannula requires a separate lumen and must be individually positioned within the tissue to be treated.

U.S. Pat. No. 5,693,029 to Leonhardt describes a catheter having a plurality of fixed-length needle assemblies that are selectively extended to pierce the walls of a lumen and inject a therapeutic agent. The therapeutic agent is delivered to the needle assemblies via a common channel. The catheter includes a balloon that is inflated to deploy the needle assemblies, and a retraction mechanism that retracts the needle assemblies once the balloon is deflated.

The foregoing devices have a number of disadvantages that limit the utility of those devices for delivering therapeutic or diagnostic agents in the heart. For example, each needle cannula in the Faxon device must be separately deployed and positioned; consequently, the use of multiple needle cannulas may be both time consuming and laborious. Similarly, because the Leonhardt device employs relatively short fixed-length needle assemblies, that device cannot be used for administering a therapeutic or diagnostic agent at various depths within the myocardium. In addition, the retraction mechanism used in the Leonhardt device inherently poses risks to the patient's health should that mechanism fail.

It therefore would be desirable to provide methods and apparatus for administering a therapeutic or diagnostic agent at multiple sites in extravascular tissue, but that does not require time consuming and laborious in-situ assembly.

It also would be desirable to provide methods and apparatus for administering a therapeutic or diagnostic agent at multiple sites in extravascular tissue at various depths.

SUMMARY OF THE INVENTION

In view of the foregoing, it is an object to provide methods and apparatus for percutaneously injecting a therapeutic agent, such as drug or angiogenic growth factor, into myocardial tissue to promote revascularization.

It is another object of this invention to provide methods and apparatus for percutaneously injecting a diagnostic agent, such as a radio-isotope or contrast agent, into myocardial tissue to enhance diagnosis of cardiac ischemia.

It is a further object of the present invention to provide methods and apparatus for administering a therapeutic or diagnostic agent at multiple sites in extravascular tissue without requiring time consuming and laborious in-situ assembly.

It is a still further object of this invention provide methods and apparatus for administering a therapeutic or diagnostic agent at multiple sites in extravascular tissue at various depths.

These and other objects of the present invention are accomplished by providing a catheter for percutaneously delivering a therapeutic or diagnostic agent to the heart comprising a sheath, a tubular member slidably disposed within the sheath, and a plurality of hollow needles coupled to the tubular member. The plurality of hollow needles have a delivery position, wherein the plurality of hollow needles are retracted within the sheath, and an extended position, wherein the plurality of hollow needles extend beyond a distal endface of the sheath and curve outwardly to penetrate extravascular tissue.

In a preferred embodiment, the catheter is adapted to be disposed in the coronary venous vasculature to inject a therapeutic or diagnostic agent at selected depths into the myocardium. The catheter preferably includes a balloon disposed on the outer sheath that may be used to apply pressure to seal the injection sites after a therapeutic or diagnostic agent is injected. Methods of using the catheter of the present invention also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention relates generally to apparatus and methods for administering a therapeutic or diagnostic agent to extravascular tissue, especially the heart. Although the invention is described hereinafter as particularly useful for administering a therapeutic and diagnostic agent to the heart, the methods and apparatus of the present invention advantageously may be used for administering therapeutic or diagnostic agents to other organs and vessels.

Figure 1:
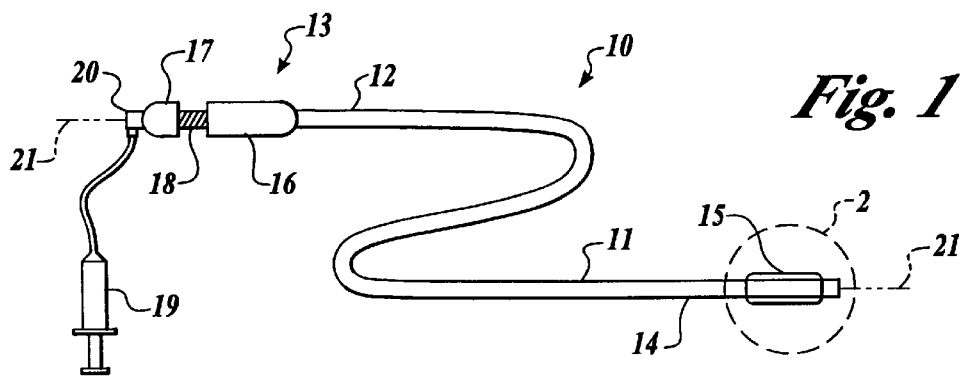
FIG. 1 is a side view of an illustrative embodiment of a catheter system constructed in accordance with the present invention.

Referring to FIG. 1, illustrative catheter 10 constructed in accordance with the present invention is described. Catheter 10 includes outer sheath 11 having proximal end 12 coupled to handle 13 and distal end 14 having inflatable balloon 15. Handle 13 includes distal portion 16 joined to outer sheath 11, and proximal portion 17, which is engaged by threads 18 with distal portion 16. Syringe 19, containing a therapeutic or diagnostic drug to be injected into a patient's tissue, is coupled to proximal portion 17 at hub 20. Guidewire 21 extends through hub 20 and out of the distal end of catheter 10. Catheter 10 preferably is 30 cm or longer, and is adapted to be percutaneously and transluminally inserted into a vessel of the patient's vasculature, such as the coronary venous vasculature.

Figure 2A:
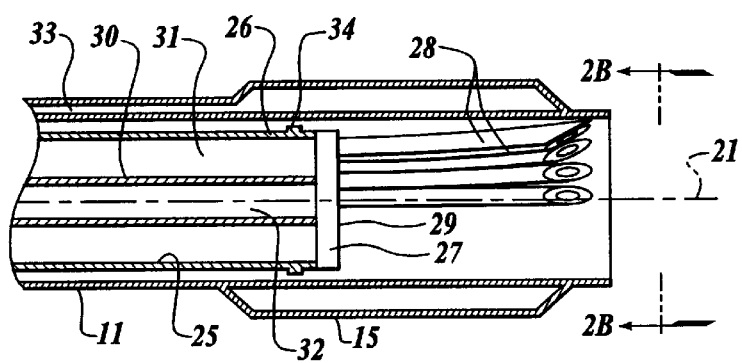
FIGS. 2A and 2B are, respectively, a cross-sectional view of the distal end of the catheter of FIG. 1, and an end view taken along view line 2B—2B of FIG. 2A, in the delivery position.
Figure 2B:
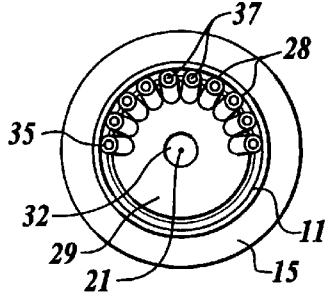

Referring now also to FIGS. 2A and 2B, tubular member 25 is arranged for sliding movement in outer sheath 11, and has a proximal end coupled to handle member 17 and distal end 26 having endcap 27. Endcap 27 has a plurality of hollow needles 28 affixed to distal endface 29. Inner member 30 is disposed coaxially within tubular member 25 to form annular lumen 31. Inner member 30 includes lumen 32, through which guide wire 21 is slidably disposed. Tubular member 25 and inner member 30 are coupled to proximal portion 17 of handle 13 so that when proximal portion 17 is rotated within distal portion 16 of handle 13, tubular member 25 and inner member 30 are extended or retracted a predetermined distance. Inflation lumen 33 couples balloon 15 to a source of inflation medium, such as a syringe (not shown), via handle 13.

Outer sheath 11, tubular member 25 and inner member 30 preferably comprise a material commonly used in catheter construction, such as polyethylene, polyvinyl chloride or polyurethane. In addition, tubular member 25 may include ring 34, formed of a layer of radio-opaque marker material, such as gold, disposed near endcap 29. Radio-opaque ring 34 may be employed to assist in orienting catheter 10 so that the distal end of tubular member 25 is aligned with a desired treatment site in the patient's vasculature.

Annular lumen 31 extends from the proximal end of catheter 10, where it is coupled to syringe 19, to endcap 29 at distal end 14. Hollow needles 28 protrude longitudinally from distal endface 29, and are in fluid communication with annular lumen 31. Hollow needles 28 preferably comprise a resilient material, such as nickel titanium or stainless steel, and are biased to curve outwardly away from the longitudinal of catheter 10 when extended beyond distal endface 36 of outer sheath 11.

Hollow needles 28 each have non-coring tip 35 and opening 37 and a lumen that communicates with annular lumen 31. Hollow needles 28 are designed to readily pierce tissue, to enable injection of a therapeutic or diagnostic agent into extravascular tissue. In accordance with one aspect of the present invention, hollow needles 28 are disposed in a semi-circular pattern, as illustrated in FIG. 2B. This arrangement ensures that when the catheter is inserted and properly oriented, for example, in the coronary sinus or great cardiac vein, the needles will extend only into the myocardium, and not puncture the circumference of the vessel adjacent the pericardial sac. Alternatively, hollow needles 28 may be arranged in a different pattern, for example to cover more or less of the circumference of endcap 29, depending upon the intended application of catheter 10.

Still referring to FIGS. 2A and 2B, when tubular member 25 is retracted proximally, for example, by rotating proximal portion 17 of handle 13 relative to distal portion 16, hollow needles 28 are retracted into outer sheath 11. When retracted in outer sheath 11, hollow needles 28 are closely bunched together, and assume a delivery position substantially parallel to a longitudinal axis of outer sheath 11. In the delivery position, outer sheath 11 prevents tips 32 from puncturing the patient's vasculature during insertion and withdrawal of catheter 10.

Figure 3A:
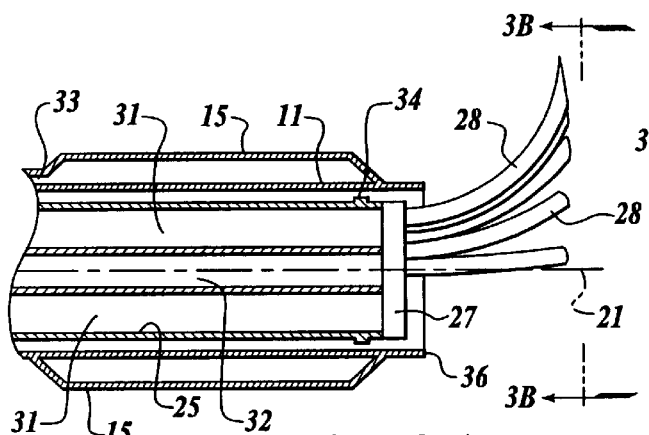
FIGS. 3A and 3B are, respectively, a cross-sectional view of the distal end of the catheter of FIG. 1, and an end view taken along view line 3B—3B of FIG. 3A, in the extended position.
Figure 3B:
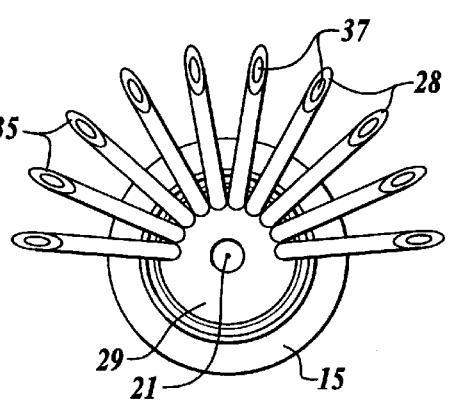

With respect to FIGS. 3A and 3B, catheter 10 is shown with hollow needles 28 in the extended position. The extended position may be attained, for example, by rotating proximal portion 17 of handle 13 relative to distal portion 16, so that tubular member 25 is translated in the distal direction. As hollow needles 28 extend beyond distal endface 36 of outer sheath 11, hollow needles curve outwardly away from the longitudinal axis of the catheter, due to the bias of the needles. Thus, as tubular member 25 slides in the distal direction, hollow needles 28 curve radially away from endcap 29 to pierce the vessel wall and surrounding tissue.

Advantageously, catheter 10 enables a clinician to adjust the depth to which tips 32 of hollow needles 28 are deployed by controlling relative motion between tubular member 25 and outer sheath 11 using handle 13. For example, handle 13 may include gradations that provide correspondence between relative motion of handle portions 16 and 17 and extension of hollow needles 28. In addition, because hollow needles 28 communicate with annular lumen 31, catheter 10 permits a therapeutic or diagnostic agent to be injected in a relatively widespread pattern without repeatedly repositioning the catheter.

Figure 4A:
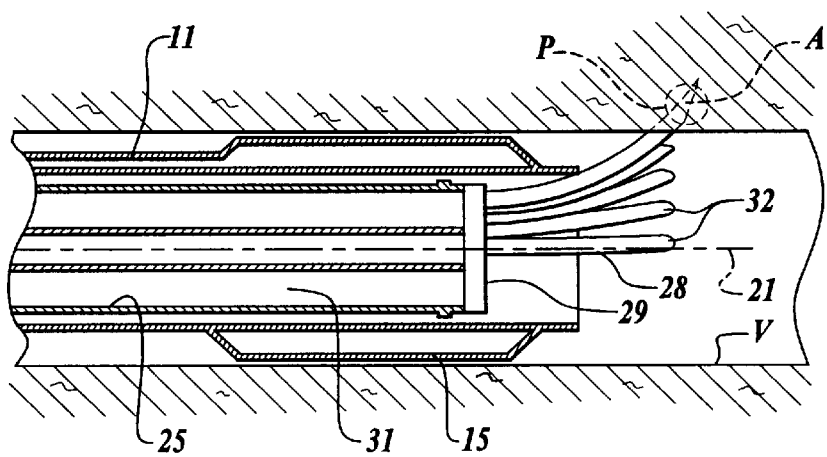
FIGS. 4A, 4B and 4C illustrate methods of using the catheter of FIG. 1 to inject a therapeutic or diagnostic agent into extravascular tissue.
Figure 4B:
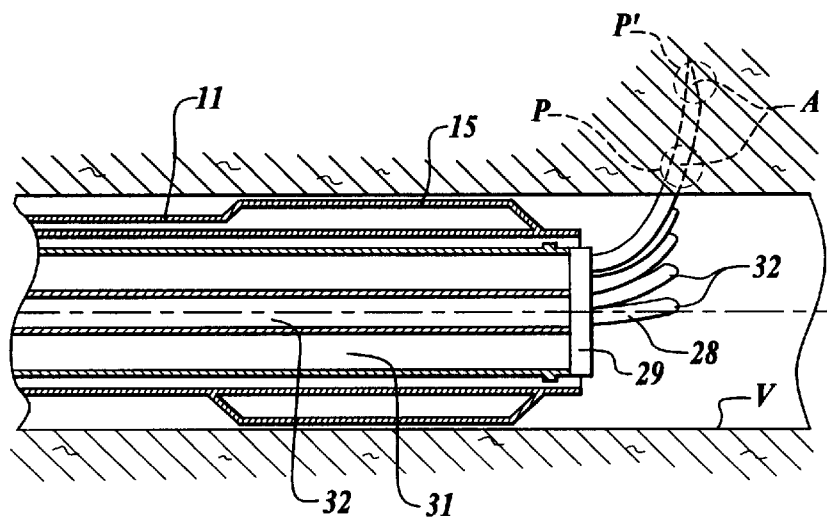

Referring now to FIGS. 4A to 4B, methods of using a catheter constructed in accordance with the present invention are described. Catheter 10 is first inserted percutaneously and transluminally into a patient's vessel V under fluoroscopic guidance. For example, if it is desired to inject an angiogenic growth factor or other bioactive agent, e.g., FGF-I or VEG-F, into the myocardium, catheter 10 may be advanced along guide wire 21 via a femoral vein, the inferior vena cava and the right atrium into the coronary sinus.

Radio-opaque ring 34 may be used to orient distal end 14 of catheter 10 adjacent a desired treatment site. Specifically, catheter 10 may be rotated so that when hollow needles 28 are extended from outer sheath 11, all of the needles pierce the epicardium, and few or none pierce the opposing vessel wall (i.e., adjacent the pericardial sac).

Once distal end 14 is properly positioned adjacent the myocardium, handle 13 is operated to translate tubular member 25 in the distal direction to extend hollow needles 28. As hollow needles 28 extend beyond distal endface 36 of outer sheath 11, the hollow needles begin to curve outwardly, so that tips 32 pierce the epicardium and myocardium adjacent to vessel V a first predetermined depth. Syringe 19 then is operated to inject therapeutic or diagnostic agent A into the tissue to form pockets P.

Handle member 13 may then be operated a second time to further extend tubular member 25, thereby causing hollow needles 28 to further penetrate into the tissue, as shown in FIG. 4B. Syringe 19 may then be actuated a second time to inject therapeutic or diagnostic agent A into the tissue to form additional pockets P'. Accordingly, handle 13 may be actuated to control the depth of penetration of hollow needles 28 to inject a therapeutic or diagnostic agent at a series of locations along a single needle track.

Once injection of the therapeutic or diagnostic agent is completed along a particular needle track, handle 13 is operated to withdraw tubular member 25 proximally into outer sheath 11, thereby causing hollow needles 28 to be retracted from the tissue and back into outer sheath 11. Once hollow needles 28 are fully retracted within outer sheath 11, catheter 10 may be removed from the patient or repositioned at another treatment site.

Figure 4C:
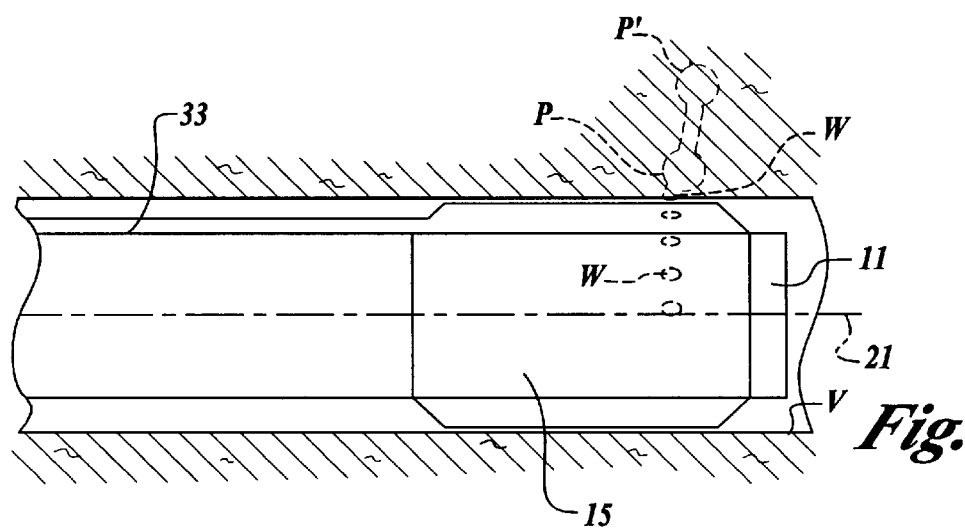

Alternatively, as illustrated in FIG. 4C, catheter 10 may be advanced over guide wire 21 so that balloon 15 is positioned adjacent puncture wounds W formed by deployment of hollow needles 28. Balloon 15 then may be inflated via inflation lumen 33 to apply a low pressure to puncture wounds W for a short interval of time, e.g., a few minutes, to seal the wounds and prevent therapeutic or diagnostic agent A from migrating along the needle track into vessel V. Balloon 15 then is deflated and catheter 10 may be removed from the patient or re-positioned at another treatment site for further injections.

Although preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. A catheter for directly delivering a therapeutic or diagnostic agent into extravascular tissue, the catheter comprising:

(a) a sheath;

(b) a tubular member slidably disposed within the sheath, the tubular member having a proximal end, a distal end, and a first lumen extending therebetween; and (c) means for both penetrating extravascular tissue, and for delivering a therapeutic or diagnostic agent into said extravascular tissue, without piercing a vessel wall, said means comprising a plurality of hollow needles arrayed around a portion of a circumference of said tubular member, each hollow needle having a sharpened tip capable of penetrating the extravascular tissue, said plurality of hollow needles being disposed on the distal end in fluid communication with the first lumen, the plurality of hollow needles having a delivery position wherein the plurality of hollow needles are disposed within the sheath, and an extended position wherein the plurality of hollow needles extend beyond a distal endface of the sheath, the plurality of hollow needles being biased to curve outwardly from the tubular member in the extended position to penetrate into the extravascular tissue, said plurality of hollow needles being configured such that when in said extended position only extravascular tissue is penetrated, while said vessel wall is not penetrated.

2. The catheter as defined in claim 1, further comprising an endcap affixed to the distal end of the tubular member, the plurality of hollow needles being affixed to a distal face of the endcap.

3. The catheter as defined in claim 2, wherein the hollow needles are arranged in a pattern on the distal face of the endcap.

4. The catheter as defined in claim 3 wherein the hollow needles are arranged in a semicircular pattern.

5. The catheter as defined in claim 1 wherein the hollow needles comprise a nickel-titanium alloy.

6. The catheter as defined in claim 1 further comprising an inner member coaxially disposed within the tubular member.

7. The catheter as defined in claim 1 further comprising a handle coupled to the sheath and tubular member to selectively extend the plurality of hollow needles to the extended position by a predetermined amount.

8. The catheter as defined in claim 1, wherein each one of the plurality of hollow needles further comprises a non-coring tip.

9. The catheter as defined in claim 1 further comprising a radio-opaque marker ring disposed on the tubular member.

10. The catheter as defined in claim 1 further comprising a balloon mounted on a distal end of the sheath.

11. A catheter for directly delivering a therapeutic or diagnostic agent into extravascular tissue, the catheter comprising:

(a) a sheath;

(b) a tubular member slidably disposed within the sheath, the tubular member having a proximal end, a distal end, and a first lumen extending therebetween;

(c) means for penetrating extravascular tissue and delivering a therapeutic or diagnostic agent into said extravascular tissue, without piercing a vessel wall, said means comprising a plurality of hollow needles arrayed around a portion of a circumference of said tubular member, each hollow needle having a sharpened tip capable of penetrating the extravascular tissue, said plurality of hollow needles being disposed on the distal end in fluid communication with the first lumen, the plurality of hollow needles being biased to curve outwardly from the tubular member in an extended position; said plurality of hollow needles being configured such that when in said extended position only extravascular tissue is penetrated, while said vessel wall is not penetrated; and (d) a handle coupled to the sheath and tubular member to selectively move the plurality of hollow needles from a delivery position, wherein the plurality of hollow needles are disposed within the sheath, to the extended position, so that in the extended position, the plurality of hollow needles extend beyond a distal endface of the sheath and penetrate the extravascular tissue.

12. The catheter as defined in claim 11, further comprising an endcap affixed to the distal end of the tubular member, the plurality of hollow needles being affixed to a distal face the endcap.

13. The catheter as defined in claim 12, wherein the hollow needles are arranged in a semi-circular pattern.

14. The catheter as defined in claim 11 wherein the hollow needles comprise a nickel-titanium alloy.

15. The catheter as defined in claim 11 further comprising an inner member coaxially disposed within the tubular member, the inner member including a lumen defining a guide wire lumen.

16. The catheter as defined in claim 11, wherein each one of the plurality of hollow needles further comprises a non-coring tip.

17. The catheter as defined in claim 11 further comprising a balloon mounted on a distal end of the sheath.

18. A method for directly delivering a therapeutic or diagnostic agent into extravascular tissue surrounding a body passageway, comprising the steps of:

(a) providing a catheter that includes a sheath, a tubular member having a lumen slidably disposed within the sheath, a handle coupled to the tubular member, and a plurality of hollow needles, each hollow needle having a sharpened tip capable of penetrating extravascular tissue, said plurality of hollow needles being disposed on a distal end of the tubular member in fluid communication with the lumen, the plurality of hollow needles being biased to curve outwardly to penetrate extravascular tissue in an extended position;

(b) operating the handle to retract the plurality of hollow needles within the Sheath;

(c) percutaneously and transluminally inserting the catheter to position a distal end of the sheath at a desired location in the body passageway;

(d) orienting the catheter so that the hollow needles are positioned to pierce the body passageway and penetrate the extravascular tissue;

(e) operating the handle so as to extend the plurality of hollow needles to pierce the body passageway and penetrate the extravascular tissue to a first depth; and (f) injecting a therapeutic or diagnostic agent through the hollow needles and into the extravascular tissue at the first depth.

19. The method of claim 18, further comprising the steps of:

(a) after injecting a therapeutic or diagnostic agent at the first depth, operating the handle to extend the plurality of hollow needles to a second depth greater than the first depth; and (b) injecting a therapeutic or diagnostic agent through the hollow needles and into the extravascular tissue at the second depth.

20. The method of claim 18, wherein the catheter further comprises a balloon; and wherein the step of operating the handle to extend the plurality of hollow needles to the first depth forms a plurality of puncture wounds, the method further comprising the steps of:

(a) after injecting a therapeutic or diagnostic agent at the first depth, operating the handle to retract the plurality of hollow needles within the sheath;

(b) repositioning the catheter within the body passageway so that the balls is aligned with the plurality of puncture wounds; and (c) inflating the balloon to apply pressure to seal the puncture wounds.

* * * * *

UNITED STATES PATENT AND TRADEMARK OFFICE
CERTIFICATE OF CORRECTION

PATENT NO. : 6,217,554 B1
DATED : April 17, 2001
INVENTOR(S) : Bert Green

It is certified that error appears in the above-identified patent and that said Letters Patent is hereby corrected as shown below:

<u>Column 8,</u>
Line 2, "Sheath" should read -- sheath --
Line 36, "balls" should read -- balloon --

Signed and Sealed this

Twenty-second Day of January, 2002

Attest:

JAMES E. ROGAN
*Attesting Officer*     *Director of the United States Patent and Trademark Office*